(12) United States Patent
Wilson et al.

(10) Patent No.: US 10,588,826 B2
(45) Date of Patent: Mar. 17, 2020

(54) MEANS FOR MONITORING COMPLIANCE, FACILITATING AUTOMATIC DISPENSING AND CHILDPROOFING STRIP PACKAGED MEDICATIONS

(71) Applicant: INTELLIGENT DEVICES SEZC INC., Grand Cayman (KY)

(72) Inventors: Allan Wilson, Ottawa (CA); Dean Brotzel, Ottawa (CA); Michael Petersen, Ottawa (CA)

(73) Assignee: INTELLIGENT DEVICES SEZC INC., Grand Cayman (KY)

(*) Notice: Subject to any disclaimer, the term of this patent is extended or adjusted under 35 U.S.C. 154(b) by 0 days.

(21) Appl. No.: 15/524,532

(22) PCT Filed: Nov. 4, 2015

(86) PCT No.: PCT/CA2015/051131
§ 371 (c)(1),
(2) Date: May 4, 2017

(87) PCT Pub. No.: WO2016/070272
PCT Pub. Date: May 12, 2016

(65) Prior Publication Data
US 2017/0312183 A1    Nov. 2, 2017

(30) Foreign Application Priority Data

Nov. 4, 2014   (CA) ........................................ 2869491
Nov. 19, 2014  (CA) ........................................ 2871873

(51) Int. Cl.
*A61J 7/04*     (2006.01)
*A61J 7/00*     (2006.01)
(Continued)

(52) U.S. Cl.
CPC ............. *A61J 7/049* (2015.05); *A61J 7/0084* (2013.01); *B65B 61/007* (2013.01); *B65D 73/02* (2013.01);
(Continued)

(58) Field of Classification Search
CPC ....... A61J 7/049; A61J 7/0084; B65B 61/007; B65D 83/0841; B65D 79/00; B65D 73/02
(Continued)

(56) References Cited

U.S. PATENT DOCUMENTS 3,450,306 A * 6/1969 Gill ........................... A61J 7/04
                                                  221/71
3,746,017 A * 7/1973 Casselman ........... A61C 15/046
                                                  132/325
(Continued)

FOREIGN PATENT DOCUMENTS

CA      2528797      6/2007
CA      2816103      1/2014
(Continued)

OTHER PUBLICATIONS

International Search Report and Written Opinion in corresponding PCT application serial No. PCT/CA2015/051131, dated Feb. 4, 2016, 13 pp.
(Continued)

*Primary Examiner* — Rakesh Kumar
(74) *Attorney, Agent, or Firm* — Caseiro Burke LLC; Chris A. Caseiro (57) ABSTRACT

There is provided an apparatus for monitoring compliance, facilitating automatic dispensing and childproofing strip packaged medication. In one embodiment a dispenser advances a packet, controls advancement of the packet and detects the presence and absence of the packet, including electronic circuitry for recording events. A replicate for strip
(Continued)

package medication can have packets with an open conductive trace, each packet being rupturable at a location to interrupt conductivity of the conductive trace. When the conductive trace of one of the packets completes an external circuit, the circuit is interrupted when the packet is ruptured. In another aspect, each packet has a tuned antenna that is tuned to an external transceiver which detects the detuning of each antenna. In a method of making a replicate for strip package medication, conductive ink is printed on a surface of each packet of the replicate and longitudinal edges of the replicate are reinforced.

13 Claims, 8 Drawing Sheets

(51) Int. Cl.
  *B65B 61/00* (2006.01)
  *G06F 19/00* (2018.01)
  *G06Q 50/22* (2018.01)
  *B65D 73/02* (2006.01)
  *B65D 79/00* (2006.01)
  *B65D 83/08* (2006.01)

(52) U.S. Cl.
  CPC ......... *B65D 79/00* (2013.01); *B65D 83/0841* (2013.01); *G06F 19/3462* (2013.01); *G06Q 50/22* (2013.01); *A61J 2200/30* (2013.01); *A61J 2205/20* (2013.01); *A61J 2205/50* (2013.01); *A61J 2205/60* (2013.01)

(58) Field of Classification Search
  USPC ............. 221/4, 18, 3, 25, 26, 7, 73, 85
  See application file for complete search history.

(56) References Cited

U.S. PATENT DOCUMENTS

| | | | |
|---|---|---|---|
| 5,199,452 A * | 4/1993 | Cheng | A61C 15/043 132/323 |
| 5,573,022 A * | 11/1996 | Winters | A61C 15/043 132/323 |
| 5,751,661 A | 5/1998 | Walters | |
| 6,098,835 A * | 8/2000 | DeJonge | B65D 83/0463 206/531 |
| 6,244,462 B1 | 6/2001 | Ehrensvard et al. | |
| 6,324,123 B1 | 11/2001 | Durso | |
| 6,616,035 B2 | 9/2003 | Ehrensvard et al. | |
| 6,628,199 B1 | 9/2003 | Ehrensvard et al. | |
| 6,707,763 B2 | 3/2004 | Osberg et al. | |
| 7,113,101 B2 | 9/2006 | Petersen et al. | |
| 7,170,409 B2 | 1/2007 | Ehrensvard et al. | |
| 7,178,417 B2 | 2/2007 | Petersen et al. | |
| 7,213,604 B2 * | 5/2007 | Romine | A61C 15/043 132/325 |
| 7,408,843 B2 | 8/2008 | Brandon | |
| 7,616,116 B2 | 11/2009 | Ehrensvard et al. | |
| 7,772,974 B2 | 8/2010 | Ehrensvard et al. | |
| 8,196,774 B1 * | 6/2012 | Clarke | A61J 7/0409 221/13 |
| 9,453,832 B2 * | 9/2016 | Uenosono | G01N 33/48785 |
| 2001/0017817 A1 * | 8/2001 | De La Huerga | A61J 1/035 368/10 |
| 2005/0258182 A1 * | 11/2005 | Anderson | A61M 15/0045 221/7 |
| 2007/0125474 A1 * | 6/2007 | Barker | B65H 35/0033 156/71 |
| 2009/0301925 A1 * | 12/2009 | Alloro | G06F 19/3462 206/534 |
| 2010/0066509 A1 | 3/2010 | Okuizumi et al. | |
| 2011/0155756 A1 * | 6/2011 | Ballard | B65D 83/0463 221/78 |
| 2013/0066463 A1 * | 3/2013 | Luoma | A61J 1/035 700/232 |
| 2013/0175286 A1 * | 7/2013 | Barrett | A61J 1/035 221/1 |
| 2013/0299381 A9 * | 11/2013 | Luciano, Jr. | A61J 1/03 206/534 |
| 2017/0158415 A1 * | 6/2017 | Choi | B65H 1/12 |
| 2017/0312183 A1 * | 11/2017 | Wilson | A61J 7/0084 |

FOREIGN PATENT DOCUMENTS

| | | |
|---|---|---|
| CA | 2821616 | 1/2014 |
| WO | WO0007904 | 2/2000 |
| WO | WO03055769 | 7/2003 |
| WO | WO2004028438 | 4/2004 |
| WO | WO2006076806 | 7/2006 |
| WO | WO2009000384 | 12/2008 |
| WO | WO2009000425 | 12/2008 |

OTHER PUBLICATIONS

International Preliminary Report on Patentability in corresponding PCT application serial No. PCT/CA2015/051131, dated Feb. 17, 2017, 8 pp.

Statement regarding no translation of three non-English foreign patent references, Jun. 8, 2017, 1 pp.

* cited by examiner

MEANS FOR MONITORING COMPLIANCE, FACILITATING AUTOMATIC DISPENSING AND CHILDPROOFING STRIP PACKAGED MEDICATIONS

TECHNICAL FIELD

The present invention relates to a means of monitoring patient compliance with strip packaged medication; a means of facilitating automated dispensing of strip packaged medication; and a means of incorporating child resistance (CR) into strip packaged medication.

BACKGROUND

Strip packaging of single and multiple unit dose medications comprises a large and growing means of packaging medications for dispensing. Currently widely used in the hospital and managed care industries, strip packaging is now entering the general pharmacy and home care areas. For institutions it has the advantages of low cost and the potential for automated dispensing. As currently formulated it poses problems in pharmacy and home care applications.

Strip packaged medication typically comprises a cellulose or polymer sheet that is folded over on itself and sealed to capture either a single medication dose or multiple doses in a unit dose medication packet. At the time of dosing the patient tears the pouch open and takes the medication. Organizing multiple medication doses in a single packet has significant implications for patient compliance.

Three problems are associated with strip packaged medication:
1) patient compliance with strip packaged medication is problematic
2) strip packaged medication is poorly suited to automated dispensing, and
3) strip packaged medication is not child resistant (CR).

Medications comprise a costly component of health care. To optimize their effectiveness they are required to be taken at specific intervals based on their pharmacokinetics. It is widely accepted that patients are poorly compliant with their prescriptions and that lack of compliance results in enormous costs to health care systems. Various prior solutions (e.g. U.S. Pat. Nos. 7,113,101; 7,178,417; 6,628,199; 6,244,462; 7,170,409; 6,616,035; 7,616,116; 7,772,974; Can. Pat. No. 2,816,103, and others) have described means of determining patient compliance electronically, but these have focused on medication dispensed in blister packages. Other prior art (e.g. U.S. Pat. Nos. 5,751,661; 6,324,123; 6,707763; 7,408,843) teaches compliance monitoring for medications packaged in vials and bottles.

Strip packaging of single and multiple unit dose medications comprises a large and growing means of packaging medications for dispensing. Strip packaging offers low cost, convenience to the patient and flexibility. Strip packaged medication comprises a cellophane or polymer sheet that is folded over on itself and sealed to capture either a single medication dose or multiple doses of similar or dissimilar medications in a unit dose medication packet. Patient and dosing information is printed on the packets, which form continuous replicates of any length depending on the application. The replicate may or may not be inserted in a paperboard container to facilitate inventory control, automated dispensing and convenience to the user. Replicates may also have perforations between packets to facilitate removal. At the time of dosing the patient tears off the distal packet, opens the packet, and takes the medication contained therein.

Currently widely used in hospitals and managed care facilities, strip packaging is now entering the general pharmacy and home care areas. For institutions it has the advantages of low cost and the potential for automated dispensing as the size of the dispenser is of little consequence. In these environments large, bulky replicates are the norm. However, for general pharmacy and home care applications there are a number of problems.

As is widely taught for other medication formats such as blister packages and vials, patient compliance with recommended dosing regimens is poor. It is desirable to know about poor compliance so it can be remediated. When used in general pharmacy and home care applications compliance is also problematic with strip packaged medication.

Patient compliance is problematic for strip packaged medication as with other (e.g. vial, blister package) dispensing formats. There is currently no means available to capture patient compliance with strip packaged medication. This is in large part due to the materials used (typically very thin, cheap, flimsy polymer or cellophane) and the form factor (long and thin).

There is a need for a means of capturing patient compliance with strip-packaged medication.

There is also a trend toward automated and robotic dispensing of medications driven by economics and the high incidence of medication errors where drugs are dispensed manually. Automated dispensing of strip packaged medication is not a problem in large institutions as space is not critical. The current generation of robotic dispensers for strip packaged medications is large and bulky to accommodate the bulk of strip packaged medications.

There is a need for a format for strip packaged medication that lends itself to compact machines for automated dispensing for general pharmacy, and to facilitate patient use, as the long, thin shape of the format does not readily lend itself to compacting by rolling or fan folding.

Hospitals and managed care facilities are not required to have child resistant (CR) packaging, something that is mandated for general pharmacy, home care and clinical trials. Current strip packaged medication does not meet CR specifications, creating a barrier to its more widespread use.

There is a need for a CR function in association with strip packaged medication

SUMMARY OF THE INVENTION

The present invention relates to a means of monitoring patient compliance with strip packaged medication; a means of facilitating automated dispensing of strip packaged medication; and a means of incorporating child resistance (CR) into strip packaged medication.

The present invention further relates to a means of incorporating electronic compliance monitoring (ECM) into strip packaged medication formats.

Unit dose strip packaging involves enclosing one or more tablets, capsules or other medication formats in a sealed packet, which is torn open by the user to release the contents at the time of dosing. The packet is typically made of cellophane but can also be of polymer, aluminum foil or other packaging materials. The individual packets form a continuous replicate and are torn off the distal end of the replicate for dispensing.

In one aspect of the present invention, continuous strips are added along longitudinal edges of any strip package format. The strips may be reinforced by heat sealing, being of increased thickness, or both. The strips can be perforated with recurrent patterns of guide holes that are different for the two sides of the replicate to ensure the replicate is inserted in the correct orientation. The guide holes are arranged to mesh with the sprockets of two sprocket wheels mounted at the ends of an axle as a means of controlling the dispensing of individual packets. The replicate can then be rolled or looped around a second axle (dowel) and the holes of the replicate are meshed with the guide sprockets. In one embodiment, a pair of closely spaced perforations is associated with a fixed position on the packet and this pair is meshed with a similarly closely spaced pair of sprockets on one sprocket wheel to facilitate indexing of the replicate to the dispenser. The sprocket wheel axle and the dowel around which the replicate is looped or rolled are snapped into position in a plastic dispenser frame that is designed to be reusable and can if desired be made of biodegradable polymer or other materials.

This mechanism may be constructed as a unit with a framework containing removable and replaceable components such as the axle, dowel, sprocket wheels battery and Printed Circuit Board (PCB) tag. The plastic dispenser frame in one aspect can be inserted into a cover or sleeve made of paperboard or other material and held in place by adhesive or friction fit. The cover can be used to display advertising or prescription information and is designed to be replaced each time the plastic dispenser is refilled.

In one embodiment the sprocket wheels can be replaced by two pairs of pinch rollers situated to grip the edges of the replicate. The rollers are comprised of a high friction material such as rubber or silicone to facilitate advancement of the replicate during dispensing. The use of pinch rollers would obviate the need for perforations in the edges of the replicate.

The dispenser preferably has a removable PCB tag comprising a battery, Computer Processing Unit (CPU), memory and wireless communications means (e.g.: RFID, NFC, Bluetooth, SigFox, GSM). In one aspect it also preferably has two flexible contact sensors oriented to bridge the gap between the ends of the conductive trace printed or otherwise affixed to the upper surface of each packet. The PCB tag is located in the dispenser so as to bring its sensors in contact with the ends of the conductive trace on the surface of the packet when it is in position for dispensing. Each packet may have a u-shaped conductive trace that, when in the dispensing position, makes a closed circuit via the contact sensors on the PCB tag and the CPU circuitry which monitors if the circuit is open or closed and records the time of changes in conductive status in its memory.

In another aspect, the sprocket axle achieves only a 180 degree revolution at a time. To the inboard sides of the sprocket wheels can be mounted stops that engage with corresponding stops mounted on the interior aspect of two flexible, partially cut out child resistant (CR) tabs in the sides of the dispenser housing. The tabs and stops can be arranged in such a way that simultaneously pressing both tabs inward releases the engagement of the stops and allows the sprocket wheel to make a further 180 degree revolution At that point the depressed CR tab stops engage with a second set of stops fixed to the axle and stop the rotation in the dispensing position.

In use, for example, the dispenser may be assembled to contain a rolled replicate and dispensed to the patient along with relevant instructions. When initialized the end of the distal replicate may be accessible at the dispensing end of the dispenser. In this example, when a dose is required the patient depresses the CR tabs and pulls the replicate out until it stops, which position is designed to leave part of the distal replicate inside the dispenser for support. In this position the contact sensors on the PCB tag close the circuit for that packet and the CPU can record the time if it is of interest. The patient can then tear open the packet that is partially protruding from the dispenser and break the circuit. The CPU detects this, interprets it as a dosing event and records the time. The process may be repeated for successive doses. When opened, the contents of the packet can drop into the dispenser's pill tray, for example, from which they may be retrieved and taken in accordance with the prescription.

In another embodiment the dispenser's PCB tab is equipped with an RF transceiver instead of the two contact sensors. Each packet of the replicate has printed or otherwise attached to its surface an RF antenna tuned to the transceiver. As described previously, the packet may be moved into position by traction on the distal end of the replicate and by the sprocket wheel control mechanism. When the distal packet moves into the dispensing position its antenna comes into close proximity with the receiver module mounted on the PCB tag and the receiver detects the field. The antenna is oriented on the packet so its architecture is disrupted when the user tears the packet open, detuning it. The resulting loss of the RF signal is detected by the receiver module and the CPU may record it as an opening event.

Irrespective of the mechanism used, the CPU for example, can determine when a packet is moved into place, when a packet is opened, and if two consecutive packets are removed from the package without one of them being opened. To achieve this the user would have to pull one packet into place and then, without opening it, press on the CR tabs and pull out a second packet.

Upon returning to the pharmacy or other facility for renewal of the prescription the compliance data can be downloaded by RFID, NFC, or Bluetooth or similar data transmission protocols to a computer or smart device. The compliance data can be displayed graphically and used by the pharmacist or other health care worker to counsel and motivate the patient to be more compliant. The data can also be stored for subsequent analysis either on a local computer or remote (cloud) server.

Although downloading the compliance data at the time of prescription renewal visits will be adequate for most clinical scenarios, in a variation of the invention the data can be downloaded, displayed and stored in real time using GSM and/or Wi-Fi with Bluetooth, SigFox or other connectivity protocols.

In one aspect, the CR feature results from the stops on the dispenser engaging the stops on the sprocket wheels. To disengage the stops the user must press simultaneously on the two CR tabs on the side of the dispenser, bending the tabs inward and releasing the stops. The degree of child resistance can be adjusted, for example, by increasing the resistance of the tabs to bending by making the cut out lever on the dispenser shorter, by making the dispenser wider and thus increasing the difficulty of pressing the two buttons simultaneously, by changing the distance the tab stops must move to disengage from the sprocket wheel stops or by other similar mechanisms.

In a variation of the CR function the sprocket wheel release mechanism may be a solenoid that prevents the sprocket from advancing until the CR tabs described are pressed, activating the solenoid to let the sprocket wheel advance and allowing the next cycle to begin.

In a further embodiment the dispenser may be equipped with a solenoid and a CPU with timing means as a locking or safety feature. When a dose is dispensed in the usual way the solenoid is locked preventing further dispensing until the time of the next prescribed dose.

The use of a plastic dispenser with or without a cardboard cover facilitates automatic or robotic dispensing of unit or multi-dose medication as for example by vending machine type robotics by permitting stacking in any orientation for storage prior to dispensing.

To facilitate robotic or other automated dispensing it may be desirable to optimize the dimensions of the packets and the dispenser.

The dispenser and/or its components can be made of biodegradable polymers or other materials to minimize environmental impact.

In situations such as clinical trials or automated dispensing of generic drugs where longer shelf life is required the use of more stable polymers or aluminum foils for the strip package may be used.

In one embodiment, a unique ID number encrypted in each CPU can facilitate track and trace for the dispenser associated with that PCB tag.

In one aspect of the present invention there is provided a dispenser comprising advancing means for advancing a packet of a replicate for strip package medication into a dispense position; child resistant means for preventing the advancing means from advancing the packet; and detection means for detecting dispensing of the packet.

In another aspect of the present invention there is provided a replicate for strip package medication comprising a plurality of packets, each containing the medication therein, each having an open conductive trace, and each packet being rupturable at a location to interrupt conductivity of the conductive trace; whereby when the conductive trace of one of the packets completes an external circuit, the circuit is interrupted when the packet is ruptured.

In a further aspect, the replicate further comprises tear guides to facilitate rupture of each package.

In yet a further aspect, the replicate further comprises a reinforced edge containing perforations therein. In yet a further aspect, each packet contains a set of double perforations in the reinforced edge.

In yet a further aspect, the replicate further comprises opposing reinforced edges containing perforations therein. In yet a further aspect, each packet contains a set of double perforations in one of the opposing reinforced edges.

In another aspect of the present invention there is provided a replicate for strip package medication comprising: a plurality of packets, each containing the medication therein, each having a tuned antenna, and each packet being rupturable at a location to detune the antenna; whereby each antenna is tuned to an external transceiver which detects the detuning of each antenna.

In another aspect of the present invention there is provided a method of making a replicate for strip package medication comprising the steps of printing conductive ink on a surface of each packet of the replicate; and reinforcing longitudinal edges of the replicate.

In a further aspect of the method, the step of reinforcing the longitudinal edges includes heat sealing the edges.

In a further aspect of the method, the step of reinforcing the longitudinal edges includes increasing the thickness of the edges.

In a further aspect, the method further comprises the step of perforating the edges with perforations.

In a further aspect of the method, the step of perforating the edges involves adding a double perforation in one edge of each packet.

In a further aspect of the method, the conductive ink is formed as a tuned RF antenna.

In a further aspect of the method, the conductive ink is formed in a u-shape.

BRIEF DESCRIPTION OF THE DRAWINGS

The invention will be further understood from the following description with reference to the attached drawings.

DETAILED DESCRIPTION OF PREFERRED EMBODIMENTS

Figure 1:
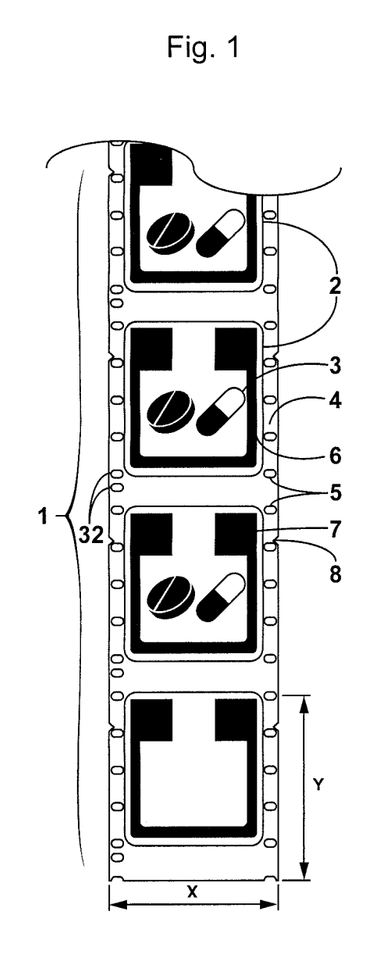
FIG. 1 shows a strip package replicate with packets, contents and heat sealed and perforated double thickness strips on both sides of the longitudinal dimension.

FIG. 1 shows a section of a strip packet replicate 1 comprising four packets 2 each containing one capsule and one tablet as example contents 3. The replicate shown contains a tablet and a capsule in each packet. The contents can be varied. The dimensions x, y of the packets 2 are variable according to the size of the contents and intended use, i.e. The size of the packet is variable in both dimensions.

The replicate 1 is typically made of cellophane, thin polymer or similar that may be easily torn. A common means of manufacture is to fold a continuous roll of cellophane over upon itself to enclose the contents and then heat seal it into individual packets 2.

In one aspect the guide holes may be designed to engage with guide sprockets in a polymer, paperboard or other dispenser. The asymmetry of the guide holes ensures the strip package is inserted in the correct orientation and is indexed to the dispense position.

In one aspect of the present invention the longitudinal edges 4 of the replicate 1 are continuously reinforced by heat sealing or other means with or without increasing the thickness. The longitudinal edges 4 have perforations 5 in a sequence that is repeated for each packet 2. On one of the two edges 4 more closely spaced double perforations 32 can be formed to correspond to the dispensing end of the packet 2 to be used for indexing the replicate 1 in the dispenser frame 9. The double perforations 32 also ensure that the replicate 1 is inserted in the dispenser frame 9 with the correct side up.

Tear guides 8 may be cut into the edges of the replicate 1 to facilitate tearing if desired.

On the surface of each packet there may be printed a conductive trace having larger contact pads at its ends.

Figure 2:
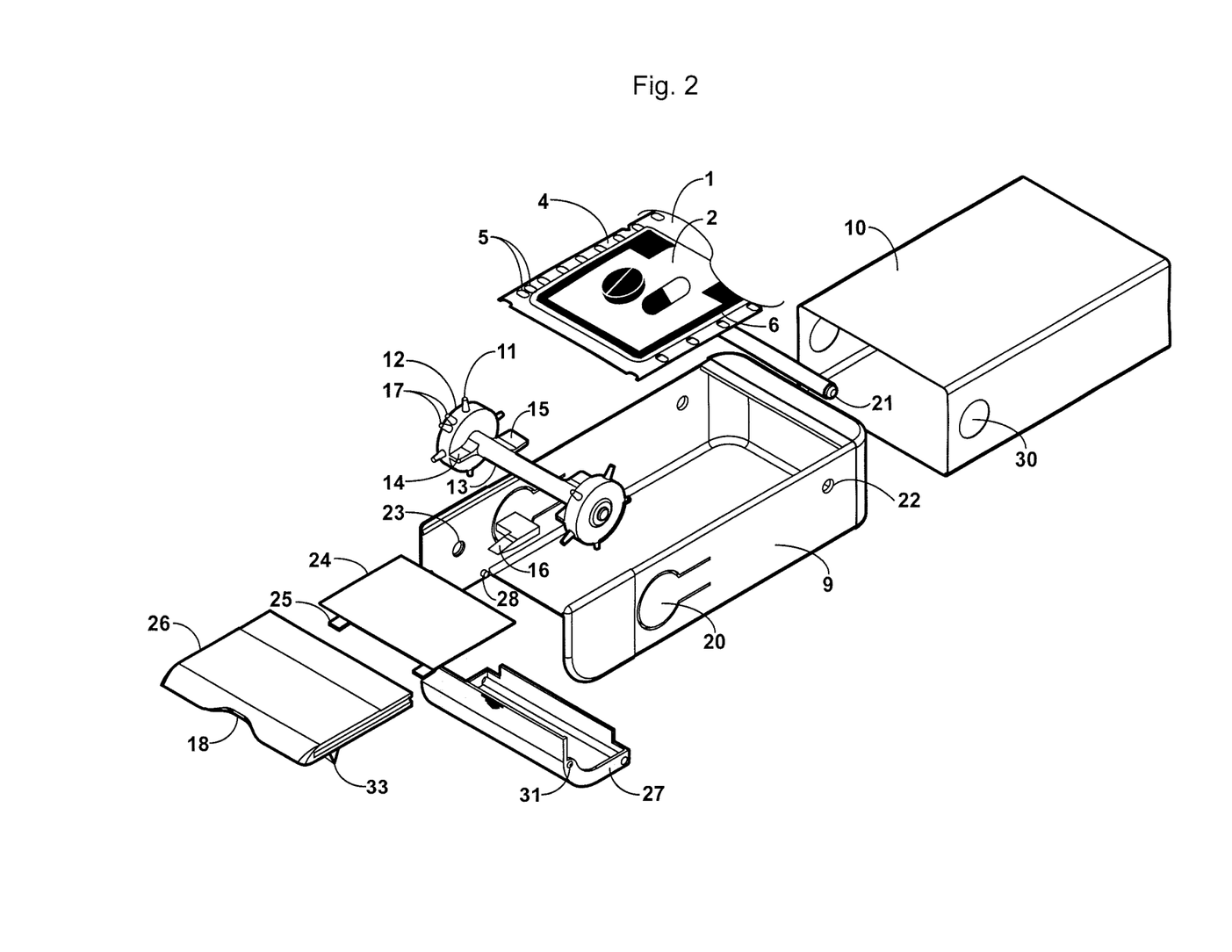
FIG. 2 is an exploded view of the dispenser showing its component parts.

FIG. 2 depicts the dispenser frame 9 and its components. The dispenser frame 9 may be made of a semi-rigid polymer and may be designed for multiple reuse.

In one embodiment the dispenser frame 9 may contain an axle 13 that locates a fixed sprocket wheel 12 at either end with a small set back to allow the ends of the axle 13 to engage with the axle holes 23 that are partially drilled through the sides of the dispenser frame 9 from the interior. The ends of the axle 13 are a snap fit to the axle holes 23 by bending the sides of the dispenser frame 9 outwards slightly.

In one aspect, the sprocket wheels 12 may have sprockets 11 to correspond with the perforations 5 on the replicate 1. One of the two sprocket wheels 12 has a double sprocket 17 more closely spaced and located so as to point upwards when the axle stops 15 are engaged with the CR tab stops 16 to define the dispense position.

As an example, the sprocket assembly may have two sets of stops. The sprocket wheel stops 14 are located on the inner aspects of the sprocket wheels 12. The axle stops 15 are attached to the axle 13 just inboard of the sprocket wheel stops 14 and oriented at 180 degrees to the sprocket wheel stops 14.

The dispenser frame 9 may include mirror-image CR tab cut outs 20 located on its longitudinal sides. These form part of the dispensing mechanism and also provide the CR feature.

In a further aspect, a CR tab stop 16 may be attached to the inner aspects of the two CR tab cut-outs 20 in the dispenser frame 9, designed and oriented to interdigitate with the sprocket wheel stops 14 to limit the rotation of the sprocket assembly to 180 degrees. Pressing the CR tab cut-outs 20 inward releases the interdigitation of the sprocket wheel stops 14 with the CR tab stops 16 and the sprocket assembly can rotate a further 180 degrees until the depressed CR tab 20 and associated stops 16 interdigitate with the axle stops 15 and stop the rotation, fixing the packet 2 in the dispense position.

FIG. 2 shows that the dispenser frame 9 may also have a guide dowel 21 that engages with the sides of the dispenser frame 9 via two dowel holes 22. The ends of the guide dowel 21 are a snap fit to the holes 22 by bending the sides of the dispenser frame 9 outwards slightly.

In another aspect, the PCB tag 24 may be located on the upper aspect of the dispenser frame 9 by friction or snap fit into a groove on the upper aspect of the frame 9. When so positioned the PCB tag's 24 contact sensors 25 are in electrical continuity with the contact pads 7 printed on the upper aspect of each packet 2 when said packet 2 is fixed in the dispense position.

FIG. 2 also shows a PCB tag cover 26 that can slide into a groove in the upper aspect of the dispenser frame 9 directly over the PCB tag 24 to provide protection. The PCB tag cover 26 may be designed with a small indentation 18 to facilitate traction on the distal end of the replicate 1 during the dispensing process. To facilitate the tearing of the packet 2 a molded cutter 33 may be incorporated into the underside of the PCB tag cover 24.

FIG. 2 also shows an optional dispense tray 27 designed to catch the packet 2 contents 3 when the packet 2 is torn open by the user. The dispense tray 27 snaps onto two bosses 28 on the inside aspect of the dispenser frame 9 and can swing down (open) in which position the contents 3 can be removed by the user. The dispense tray 27 is held in its closed position by friction fit between two small bosses 31 on the tray and two corresponding indentations on the interior aspect of the dispenser frame 9.

In another aspect, FIG. 2 further shows a disposable paperboard cover 10. This is designed to be friction or adhesive fit to the frame whose contents and mechanisms it covers and protects and may be a sleeve or a five-sided box. The cover 10 has two circular cut-outs 30 positioned over the CR tab cut-outs 20 so the latter can be depressed by the user applying pressure through the cover cut-outs 30.

Figure 3:
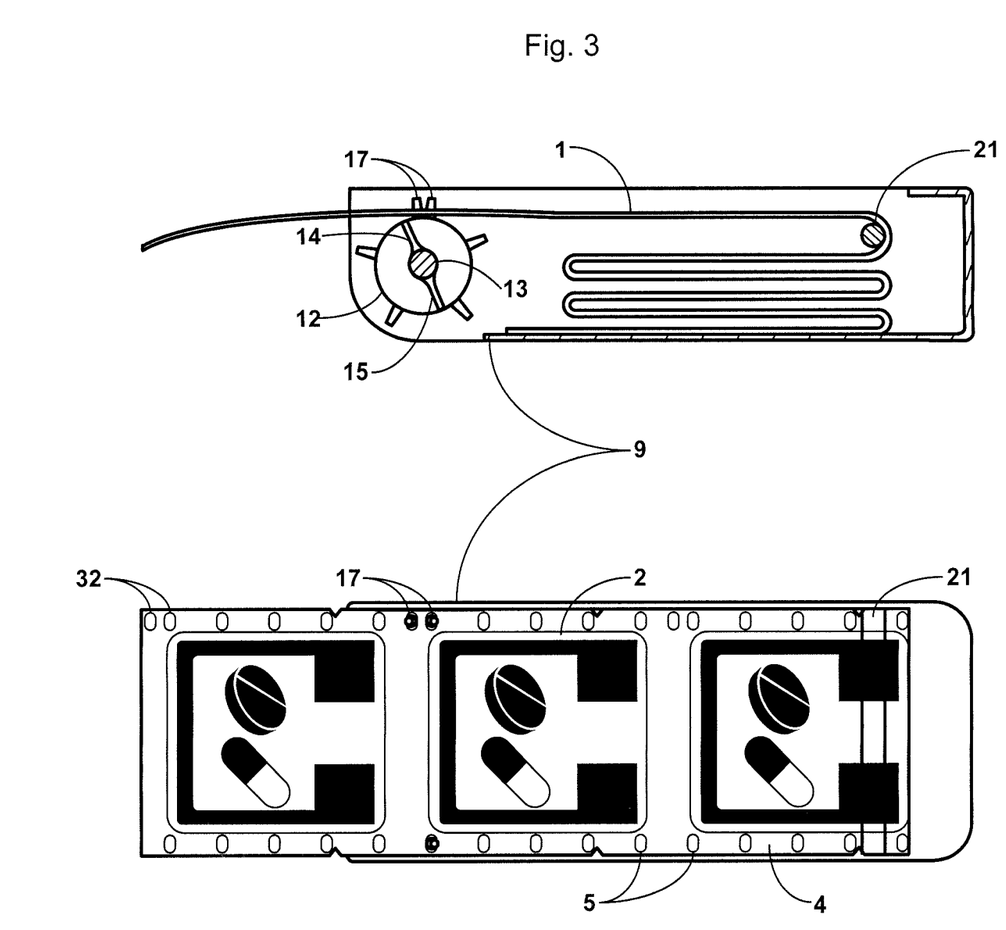
FIG. 3 shows a container with strip packaged content.

FIG. 3 shows an example of a loading and dispensing procedure in a container with strip packaged content. The replicate is fan folded and the free end is engaged with the double teeth of the sprocket to locate the distal replicate in the dispense position. In preparing the dispenser frame 9 for use, the guide dowel 21 is snapped into the dowel holes 22 by bending the sides of the dispenser frame 9 slightly outwards. The replicate 1 is fan-folded or loosely rolled to fit in the dispenser frame 9. The distal end of the replicate 1 is then looped upwards around the guide dowel 21 with the conductive traces 6 printed on the packets 2 facing up. The ends of the axle 13 of the sprocket assembly (FIG. 2) may be inserted into the axle holes 23 by bending the sides of the dispenser frame 9 slightly outwards. The sprocket assembly is rotated counterclockwise until the axle stops 15 engage the CR tab stops 16. The user presses the CR tab cut-outs 20 inward, disengaging the axle stops 15 from the CR tab stops 16 allowing the axle to rotate a further 180 degrees at which position the double sprocket 17 on one sprocket wheel 12 points upwards.

FIG. 3 shows the closely spaced double perforations 32 of the distal aspects of each packet 2 of the replicate. The double perforations 32 of the distal packet 2 are aligned over the double sprocket 17 and the remainder of the perforations 5 are engaged with the sprockets 11. This positions the distal packet 2 in the dispense position.

Figure 4:
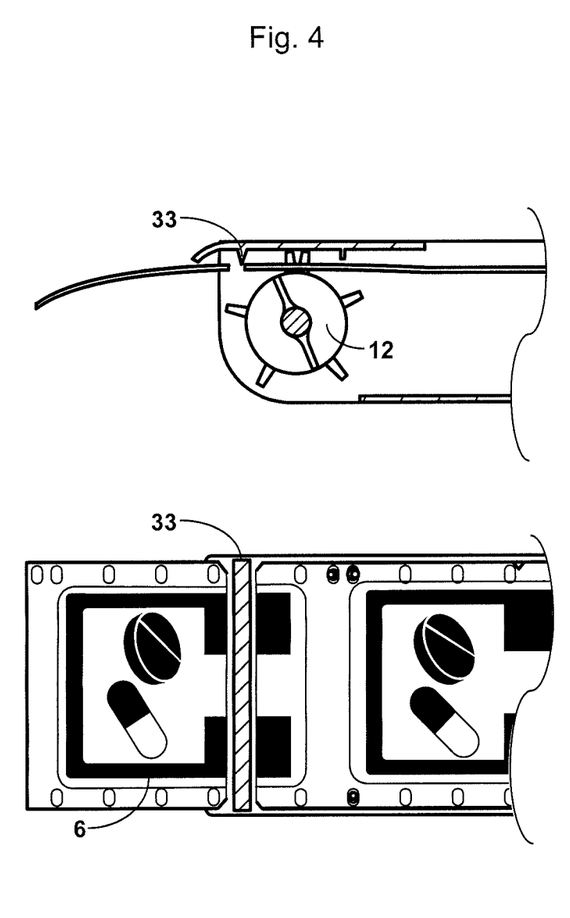
FIG. 4 shows details of the optional extrusion to facilitate dispensing which is situated on the underside of the cover to ensure that the conductive trace on the packet is broken when the packet is opened.

FIG. 4 depicts an optional cutter 33 that can be an extrusion attached to or forming part of the underside of the PCB tag cover 26 the function of which is to facilitate dispensing. It is located so as to break the conductive trace 6 on the packet 2 at the time of dispensing.

In use the user may tear the distal packet 2 open allowing the contents to drop into the dispense tray 27 from which they are retrieved. Tearing the packet 2 open breaks the circuit comprising the conductive trace 6 and PCB tag 24 mounted contact sensors 25 and the CPU detects the increase in resistance and interprets it as an opening event that infers the medication has been taken.

Figure 5:
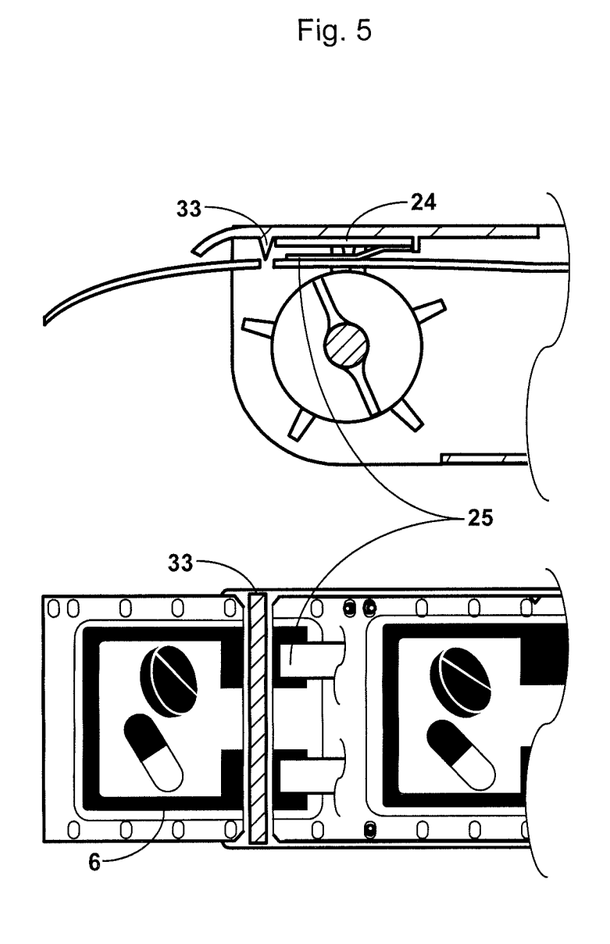
FIG. 5 shows the two friction (spring) contact sensors electrically connecting the tag and the packet when the packet is in the dispense position.

FIG. 5 shows an example of a spring loaded contact sensor 25 that provides electrical continuity between the CPU of the PCB tag 24 and the conductive trace 6 printed on the packet 2 when the packet 2 is in the dispense position. To facilitate contact between the conductive trace 6 and the contact sensors 25, the proximal ends of the u-shaped conductive trace 6 may be enlarged as shown. When the user tears the packet open the trace is broken and the tag detects the open circuit, recording the time in its memory.

Figure 6:
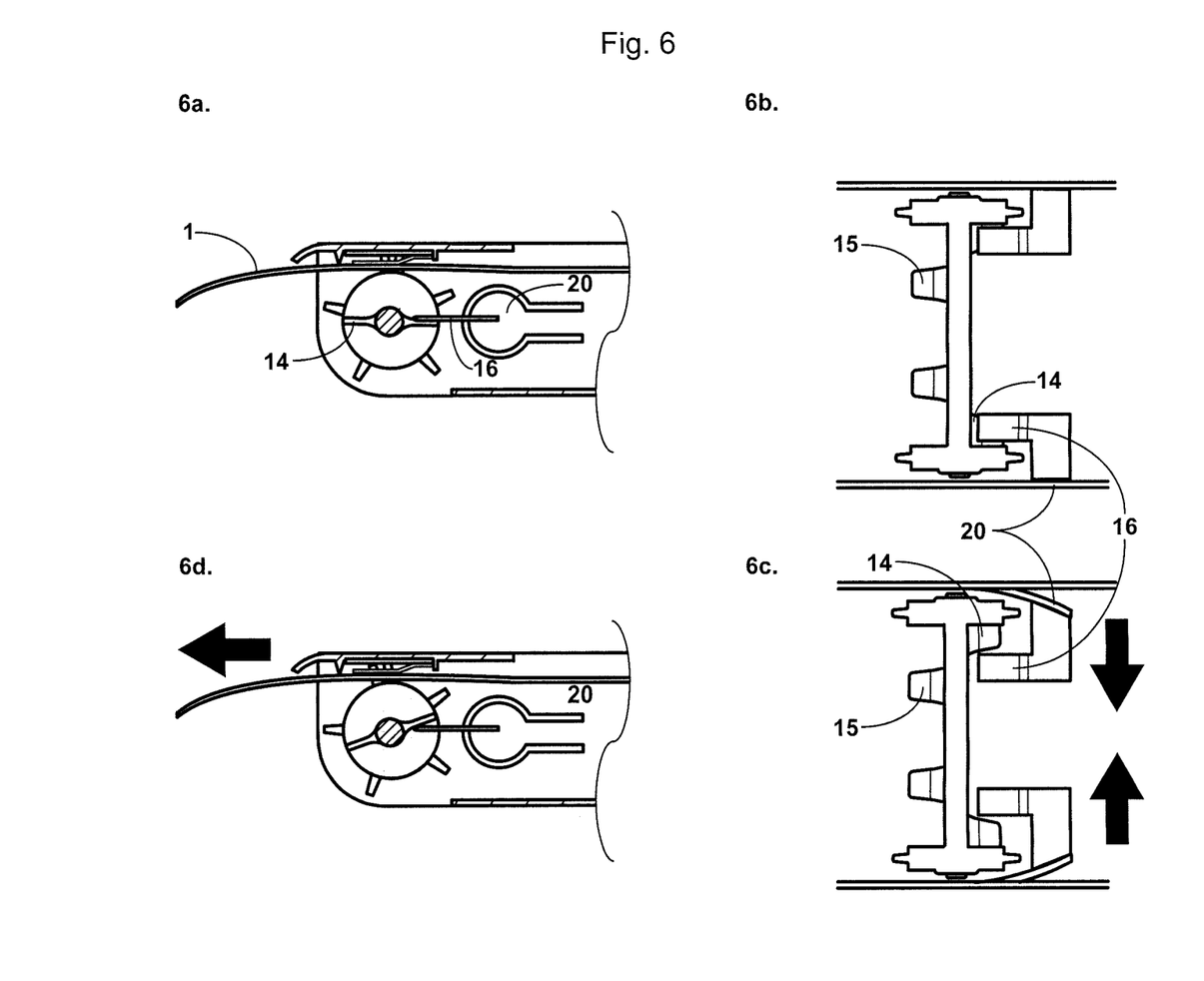
FIG. 6 details the control mechanism that locates the distal packet in the dispense position.

FIG. 6 shows the sprocket assembly dispensing control mechanism. In FIG. 6a the replicate 1 has been pulled by the user and the CR tab stop 16 has engaged the sprocket wheel stop 14, preventing further extraction of the replicate 1 from the dispenser 9. FIG. 6b is a top view showing the CR tab stops 16 engaged with the sprocket wheel stops 14 preventing further rotation of the sprocket assembly. The top view in FIG. 6c shows the position of the CR tab stops 16 when the CR tab cut-outs 20 are depressed inwards (arrows). The CR tab stops 16 have moved medially and disengaged from the sprocket wheel stops 14 allowing the sprocket assembly to rotate a further 180 degrees as shown in FIG. 6d. At that point the CR tab stops 16 engage with the axle stops 15 preventing further rotation of the sprocket assembly and fixing the distal packet 2 of the replicate 1 in the dispense position.

Figure 7:
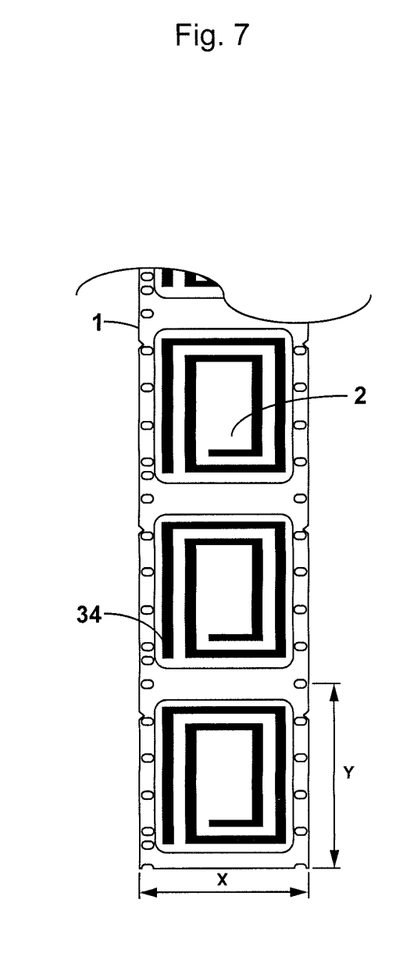
FIG. 7 shows a variation of the invention that uses RF rather than physical contact to determine the state of the packets.

FIG. 7 shows an example means of determining the position and state of the packets using radio frequency (RF). In this variation, a tuned RF antenna 34 is printed on or otherwise attached to each packet 2 with conductive ink or other conductive substance. An RF transceiver is incorporated into the PCB tag 24. The presence of the tuned RF field is detected by the receiver module of the PCB tag 24 when the antenna 34 comes into close proximity with the receiver of the PCB tag 24 at the dispense position. As for FIGS. 3 to 6 above, the packet 2 is moved into position by traction on the distal end of the replicate 1 and by the sprocket assembly. When the user tears the packet 2 open the antenna 34 is broken (detuned) and the PCB tag's 24 CPU records the time of detuning as a dispense event and a means of inferring content use.

Figure 8:
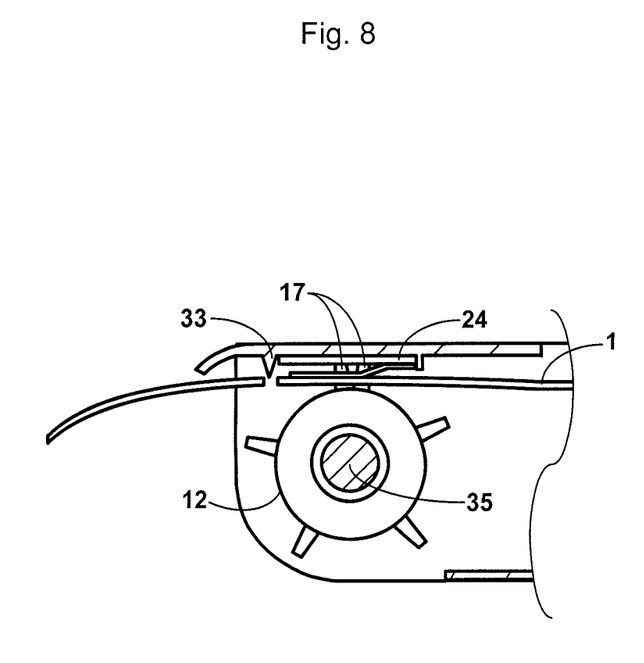
FIG. 8 shows a variation of the child resistant function in which the release mechanism is a micro solenoid that prevents the sprocket from advancing until the buttons shown in FIG. 2 are pressed, activating the solenoid to let the sprocket advance and allowing the next cycle to begin.

FIG. 8 shows a variation in which the CR function is provided by a solenoid 35 attached to the sprocket wheel 12. The solenoid 35 prevents the sprocket wheel 12 from advancing until the CR tab cut-outs 20 are pressed simultaneously, activating the solenoid 35 to let the sprocket wheel 12 advance 360 degrees allowing the next cycle to begin. In this variation axle stops 15 and sprocket wheel stops 14 are not required as the solenoid 35 performs their functions.

In a further embodiment the sprocket assembly is equipped with a solenoid 35 and the PCB tag 24 with a CPU having timing means as a locking or safety feature. When a dose is dispensed the solenoid 35 is locked preventing further dispensing until the time of the next prescribed dose.

In one embodiment the dispenser is programmed with dosing intervals or other pharmacokinetic (PK) information. The use data collected by opening events are compared to the PK data to determine the extent to which the use data are consistent with the PK data.

In a further embodiment the CPU is programmed with an algorithm to track the patient's compliance and the dispenser can display this by way of motivating the patient's behavior as, for example, continually updating, rating and displaying the patient's medication-taking compliance. This information can be displayed, for example, on the cover of the dispenser. For example, the cover can display compliance data numerically, by patterns of LEDs or LCDs (liquid crystal display), by colour changes via OLEDs and/or by symbols or other means.

In another embodiment the CPU is programmed to continually compare the most recent opening to previous openings using a dynamic algorithm and to compare the patient's compliance pattern to a preprogrammed ideal PK pattern. Using regression analysis or other widely taught trend analytical techniques the CPU develops a dynamic algorithm to predict problematic trends in the patient's compliance. Warnings and feedback can then be provided using a visual output, auditory output or tactile devices to alert the user to maladaptive medication-taking trends and potential problems.

In another embodiment the dispenser is additionally equipped with the ability to be plugged into a computer using USB or other wired protocol. The compliance data can be summarized and displayed in graphic format to motivate the patient.

In a further embodiment, the dispenser incorporates means of emitting an RF signal that permits communication with an external smart device such as a tablet or phone using RFID, Bluetooth, NFC, sigFox, qual2 or other data transmission protocol. These devices can be used to display reminders, compliance summaries or other information via apps.

In a further embodiment the dispenser incorporates the ability to communicate by GSM (Groupe Special Mobile) with devices which can be used to display reminders, compliance summaries or other information via graphic user interfaces or apps.

In a variant, other parties of interest other than the user may be given permission to access the dispenser's data via apps on smart devices or computers in the interests of monitoring the user's compliance with prescribed medication and detecting maladaptive patterns of use.

In another embodiment the dispenser can communicate wirelessly by Wi-Fi or GSM to an app forming part of a larger eHealth network from which the user and her designate(s) can access the data to receive motivational feedback and warnings about maladaptive medication-taking patterns and assessing the need for early intervention to prevent health deterioration.

The dispenser frame is reusable and can be returned to the pharmacy for reuse or retained to be reused on a subsequent refill of the same medication for the same patient. Any power source (e.g. battery) or electronic module (PCB) can be replaced as required.

It will be appreciated by one skilled in the art that variants can exist in the above-described arrangements and applications. The specific examples provided herein relate to a means of monitoring patient compliance, facilitating automated dispensing and including child resistance in strip packaged medication; however, the materials, methods of application and arrangements of the invention can be applied to other similar packaging and contents.

The scope of the claims should not be limited by the preferred embodiments set forth in the examples, but should be given the broadest interpretation consistent with the description as a whole.

What is claimed:

1. A dispenser comprising:
   an axle for advancing a packet of a replicate for strip package medication into a dispense position, wherein the axle separates two sprocket wheels having sprockets which coincide with perforations on longitudinal edges of the replicate;
   child resistant means for preventing the axle from advancing the packet; and
   a tag for detecting dispensing of the packet;
   wherein the child resistant means comprises a tab stop and a cut-out aligned with the tab stop to disengage the tab stop, and the axle comprises a sprocket wheel stop which is configured to engage the tab stop to limit rotation of the axle.

2. The dispenser of claim 1 wherein the cut-out is a deformable partial cut-out.

3. The dispenser of claim 2 wherein the axle further comprises an axle stop which is configured to engage the tab stop to limit further rotation of the axle.

4. The dispenser of claim 3 wherein the axle stop limits the rotation to a full revolution which limits advancement of the replicate by a single packet.

5. The dispenser of claim 1 wherein the tag is a removable Printed Circuit Board (PCB) tag comprising a battery, a Computer Processing Unit (CPU), memory, and wireless communication means.

6. The dispenser of claim 5 wherein the PCB tag further comprises two contact sensors.

7. The dispenser of claim 6 wherein the axle advances the packet having a conductive trace thereon so that the contact sensors have electrical continuity with the conductive trace to form a closed circuit with only the packet which is in the dispense position.

8. The dispenser of claim 7 wherein the PCB tag periodically polls for continuity of the closed circuit and detects and records when the closed circuit is broken as by dispensing.

9. The dispenser of claim 8 wherein the CPU comprises a computer readable medium storing statements and instructions thereon that when executed by a processor track compliance of a user.

10. The dispenser of claim 9 further comprising means of emitting an RF signal to transmit data related to the compliance to an external device.

11. The dispenser of claim 9 further comprising one or more of a numeric display, pattern of Light Emitting Diodes (LEDs) pattern of Liquid Crystal Displays (LCDs), colour change of an Optical Light Emitting Diode (OLED) or display of symbols for motivating the user to comply with medication instructions.

12. The dispenser of claim 11 wherein the one or more of a numeric display, pattern of LEDs, pattern of LCDs, colour change of an OLED or display of symbols warns the user of non-compliance through alert means.

13. The dispenser of claim 1 further comprising a Radio Frequency (RF) transceiver that detects a field of a tuned antenna on the packet when it is in the dispense position; wherein the tuned antenna is tuned to the RF transceiver; and wherein the RF transceiver detects a disruption in a signal of the tuned antenna when the packet is dispensed.

* * * * *